United States Patent
Omray et al.

(10) Patent No.: US 7,964,182 B2
(45) Date of Patent: *Jun. 21, 2011

(54) PHARMACEUTICAL COMPOSITIONS COMPRISING PHOSPHATE-BINDING POLYMER

(75) Inventors: Ashok Omray, Mumbai (IN); Varsha Shashank Choudhary, Mumbai (IN); Yogesh Sharad Bhide, Mumbai (IN)

(73) Assignee: USV, Ltd, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/957,810

(22) Filed: Dec. 1, 2010

(65) Prior Publication Data
US 2011/0064820 A1    Mar. 17, 2011

Related U.S. Application Data

(63) Continuation-in-part of application No. 12/620,931, filed on Nov. 18, 2009, now Pat. No. 7,846,425, and a continuation-in-part of application No. 12/377,129, filed on Feb. 11, 2009.

(30) Foreign Application Priority Data

Jan. 22, 2009    (IN) .......................... 142/MUM/2009

(51) Int. Cl.
*A61K 31/77* (2006.01)
*A61K 31/765* (2006.01)
*A61K 9/50* (2006.01)
*C08G 79/02* (2006.01)

(52) U.S. Cl. .................. 424/78.38; 424/78.35; 424/501; 528/398

(58) Field of Classification Search .................. 424/501, 424/78.38, 78.35; 528/393
See application file for complete search history.

(56) References Cited

U.S. PATENT DOCUMENTS

| | | |
|---|---|---|
| 4,605,701 A | 8/1986 | Harada et al. |
| 5,275,824 A | 1/1994 | Carli et al. |
| 5,490,987 A | 2/1996 | Shen et al. |
| 5,496,545 A | 3/1996 | Holmes-Farley et al. |
| 6,083,495 A | 7/2000 | Holmes-Farley et al. |
| 6,121,411 A | 9/2000 | Satori et al. |
| 6,362,266 B1 | 3/2002 | Buchholz et al. |
| 6,383,518 B1 | 5/2002 | Matsuda et al. |
| 6,525,113 B2 | 2/2003 | Klix et al. |
| 6,600,011 B2 | 7/2003 | McDonnell et al. |

(Continued)

FOREIGN PATENT DOCUMENTS
EP    1304104 B1    4/2003

(Continued)

OTHER PUBLICATIONS

"(logo) RENVELA® (Sevelamer Carbonate)," label (downloaded from www.fda.gov/cder/foi/label/2007/022127lbl.pdf) Food and Drug Administration (2007).

(Continued)

*Primary Examiner* — Robert A Wax
*Assistant Examiner* — Aradhana Sasan
(74) *Attorney, Agent, or Firm* — Pharmaceutical Patent Attorneys, LLC

(57) ABSTRACT

The present invention discloses pharmaceutical composition comprising phosphate binding polymers such as Sevelamer carbonate substantially free of monovalent anion other than bicarbonate anion. Particularly, monovalent anion content is less than about 0.05% (w/w). Disclosed are compositions comprising wet granulated Sevelamer carbonate free of added metal ions and/or added monovalent anion source.

19 Claims, 2 Drawing Sheets

U.S. PATENT DOCUMENTS

| | | |
|---|---|---|
| 6,696,087 B2 | 2/2004 | Matsuda et al. |
| 6,733,780 B1 | 5/2004 | Tyler et al. |
| 6,756,364 B2 * | 6/2004 | Barbier et al. ............ 514/57 |
| 7,229,613 B2 | 6/2007 | Burke et al. |
| 7,381,424 B2 | 6/2008 | MacGregor |
| 7,388,056 B2 | 6/2008 | Gopalkrishna et al. |
| 7,749,536 B2 | 7/2010 | Hrakovsky et al. |
| 2002/0054903 A1 | 5/2002 | Tyler et al. |
| 2002/0119193 A1 | 8/2002 | Le et al. |
| 2005/0131138 A1 | 6/2005 | Connor et al. |
| 2006/0251614 A1 | 11/2006 | Bhagat et al. |
| 2007/0027213 A1 | 2/2007 | Oberegger et al. |
| 2007/0110706 A1 | 5/2007 | Connor et al. |
| 2007/0190135 A1 | 8/2007 | Matsuda et al. |
| 2009/0280178 A1 | 11/2009 | Hedge et al. |
| 2010/0008988 A1 | 1/2010 | Mehta et al. |
| 2010/0137542 A1 | 6/2010 | Jobdevairakkam et al. |

FOREIGN PATENT DOCUMENTS

| | | |
|---|---|---|
| EP | 1818048 A1 | 8/2007 |
| IN | 142/MUM/2009 * | 1/2009 |
| WO | WO0121211 A1 | 3/2001 |
| WO | WO2005041900 A2 | 5/2005 |
| WO | WO2007094779 A1 | 3/2007 |
| WO | WO2009156014 A1 | 12/2009 |

OTHER PUBLICATIONS

Ritz, E., et al., "Role of Sodium Intake in the Progression of Chronic Kidney Disease," Journal of Renal Nutrition 2009, 19 (1): 61-2, (2009).

Chertow, G.M., et al., "The Effects of Sevelamer and Calcium Acetate on Proxies of Atherosclerotic and Arteriosclerotic vascular disease in hemodialysis patients," American Journal of Nephrology, 23(5): 307-314 (2003).

Mazzeo, J.R. et al., "A Phosphate Binding Assay for Sevelamer Hydrochloride by Ion Chromatography," J. Pharm. Biomed. Anal. (1999) 19, pp. 911-915.

"(logo) RENEGAL Tablets (sevelamer hydrochloride) 400 and 800 mg," Package insert (downloaded from http://www.fda.gov/cder/foi/label/2000/21179lbl.pdf), Food and Drug Administration (2000).

Schulz, W. "Sevelamer Hydrochloride," Taegliche Praxis, XX, (2001) vol. 42, No. 3, pp. 621-626.

* cited by examiner

PHARMACEUTICAL COMPOSITIONS COMPRISING PHOSPHATE-BINDING POLYMER

RELATED APPLICATIONS

This application claims priority from co-pending U.S. Ser. No. 12/995,543 filed 1 Dec. 2010, which in turn claims priority from PCT Application Serial No. PCT/IN2010/000038 filed on 22 Jan. 2010, which in turn claims priority from Indian Provisional Application No. 142/MUM/2009 filed on 22 Jan. 2009.

This application also claims priority as a continuation in part from U.S. Ser. No. 12/620,931 filed 18 Nov. 2009 (now U.S. Pat. No. 7,846,425) and co-pending U.S. Ser. No. 12/377,129 filed 11 Feb. 2009, which in turn claim priority from PCT/IN2007/000387 filed 31 Aug. 2007, which in turn claims priority from India National patent application Serial No. 1402/MUM/2006, filed 1 Sep. 2006, the contents of which are here incorporated by reference.

TECHNICAL FIELD OF THE INVENTION

The present invention relates to pharmaceutical compositions of phosphate binding polymers such as Sevelamer and any pharmaceutically acceptable salts thereof. In particular, the invention relates to pharmaceutical composition of Sevelamer carbonate and process of preparation thereof.

BACKGROUND OF THE INVENTION

Chronic kidney disease (CKD) is a progressive loss of renal function over a period of time. CKD is identified by performing a blood test for creatinine. High levels of creatinine indicates a poor glomerular filtration rate and a decreased capability of the kidneys to excrete waste products. Decreased kidney function leads to high blood pressure due to fluid overload and production of vasoactive hormones and increases the risk of hypertension or congestive cardiac failure, urea accumulation, potassium accumulation, decreased erythropoietin synthesis, edema, hyperphosphatemia due to reduced phosphate excretion and metabolic acidosis.

In End-stage renal disease (ESRD), there is total kidney failure requiring the patients to have renal replacement therapy, either dialysis or transplantation becomes necessary to maintain life. Hemodialysis involves circulation of blood through a filter on a dialysis machine where the blood is cleansed of waste products and excess water. The acid levels and the concentration of various minerals such as sodium and potassium in the blood are normalized and blood is then returned to the body.

Patients with chronic kidney disease (CKD) retain phosphorus and can develop hyperphosphatemia. Hyperphosphatemia is a condition where the serum phosphate levels are greater than 5 mg/dL in adults or 7 mg/dL in children or adolescents. If the condition persists for a long period then it leads to severe abnormalities in calcium and phosphorus metabolism resulting in calcification in joints, lungs and eyes. Hyperphosphatemia plays a significant role in the development of secondary hyperparathyroidism in renal insufficiency. Treatment of hyperphosphatemia includes reduction in dietary intake of phosphate, inhibition of intestinal phosphate absorption with phosphate binders and removal of phosphate with dialysis.

Oral administration of phosphate binders like calcium or aluminium for the treatment of hyperphosphatemia are well known in the art. Most widely used are the calcium salts such as calcium carbonate, calcium acetate, calcium citrate or calcium alginate. These calcium salts when ingested binds to the intestinal phosphate to form insoluble calcium phosphate salts such as calcium hydrogen phosphate, calcium dihydrogen phosphate or tricalcium phosphate and thus prevents the phosphate absorption. However, the drawback associated with this mode of treatment is that due to absorption of high amount of ingested calcium, the patient develops hypercalcemia which inturn results in cardiac arrhythmias, renal failure and skin and visceral calcification.

Sevelamer carbonate is a polymeric amine which binds to phosphates when administered orally. Sevelamer carbonate has the same polymeric structure as Sevelamer hydrochloride in which carbonate replaces chloride as the counterion. Sevelamer carbonate is chemically poly (allylamine-co-N,N'-diallyl-1,3-diamino-2-hydroxypropane) carbonate salt. Structure of Sevelamer carbonate is as represented,

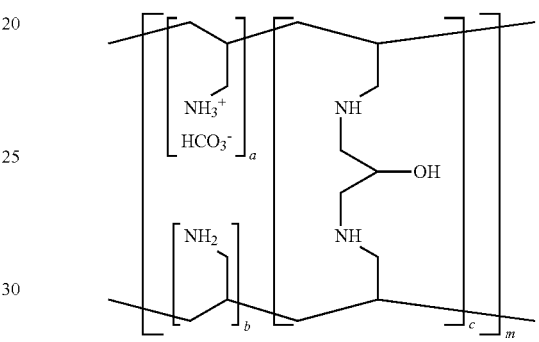

where
a, b=number of primary amine groups a+b=9
c=number of crosslinking groups c=1
m=large number to indicate extended polymer network Sevelamer carbonate is developed by Genzyme Corporation and marketed under the brand name RENVELA® Sevelamer Carbonate. The prescribing information for RENVELA®Sevelamer Carbonate is available on www.fda.gov/cder/foi/label/2007/0221271bl.pdf. RENVELA® Sevelamer Carbonate is indicated for the control of serum phosphorus in patients with chronic kidney disease (CKD) on dialysis and not on dialysis. RENVELA® Sevelamer Carbonate contains Sevelamer carbonate, a non-absorbed phosphate binding crosslinked polymer, free of metal and calcium. RENVELA® Sevelamer Carbonate 800 mg tablets contain 800 mg of Sevelamer carbonate on an anhydrous basis, microcrystalline cellulose, hypromellose, diacetylated monoglycerides, sodium chloride and zinc stearate.

Sevelamer carbonate taken with meals has been shown to control serum phosphorus concentrations in patients with CKD who are on dialysis. Sevelamer carbonate contains multiple amines separated by one carbon from the polymer backbone. These amines exist in a protonated form in the intestine and interact with phosphate molecules through ionic and hydrogen bonding. Sevelamer carbonate binds the phosphorus in the gastrointestinal tract to facilitate phosphorus excretion in feces, thereby inhibiting phosphorus absorption from the gut and thereby lowering the plasma phosphorus concentration.

Patients with end-stage renal disease (ESRD) retain phosphorus which lead to development of hyperphosphatemia. Control of phosphorus is the primary goal in the care of patients with end-stage renal disease (ESRD). Sevelamer carbonate controls the serum phosphorus in patients with ESRD who are on hemodialysis, without increasing serum calcium levels or contributing an excess calcium load.

U.S. Pat. No. 5,496,545 discloses phosphate-binding polymers that are orally administered and useful for the treatment of hyperphosphatemia.

U.S. Pat. No. 6,083,495 discloses a class of anion exchange polymers having improved phosphate binding properties and a method of removing phosphate from a patient by ion exchange involving oral administration of a therapeutically effective amount of a composition containing at least one phosphate-binding polymer.

U.S. Pat. No. 6,696,087 discloses a phosphate-binding polymer tablet that contains a large amount of the phosphate-binding polymer having an average particle size of 400 μm or less, preferably 250 μm or less, containing particles of 500 μm or less, preferably 300 μm or less, in size at a ratio of 90% or more and having a moisture content of 1 to 14%, together with crystalline cellulose and/or low substituted hydroxypropylcellulose.

U.S. Pat. No. 6,733,780 discloses a direct compression polymer tablet core containing at least about 95% by weight of an aliphatic amine polymer and a method of producing such a tablet core involving the steps of hydrating the aliphatic amine polymer to the desired moisture level; blending with additives in amounts such that the polymer comprises at least about 95% by weight of the resulting blend; and compressing the blend to form the tablet core.

WO2006050315 discloses Sevelamer carbonate compositions containing monovalent anion that can prevent or ameliorate acidosis, in particular acidosis in patients with renal disease. According to this document, addition of a monovalent anion source to Sevelamer carbonate prevents the increase in the disintegration time of the tablets and increases the shelf life.

WO2007094779 discloses compositions containing aliphatic amine polymers prepared by spray granulation method.

Health care professionals have recognized the detrimental effects of high sodium intake on blood pressure control, congestive heart failure and fluid balance in patients with chronic kidney disease. Further, limiting the intake of commonly used metal salts such as those of sodium, calcium, potassium, aluminium or magnesium will benefit the patients with chronic kidney disease and on haemodialysis.

A study on role of salt intake in the progression of chronic kidney disease has been described in 'Journal of Renal Nutrition' by E. Ritz et. al. [Reference: 'Role of sodium intake in the progression of chronic kidney disease' by Department of Internal Medicine, Ruperto Carola University, Heidelberg, Germany; cited in Journal of Renal Nutrition 2009 January; 19(1):61-2. by E. Ritz et. al.]

In such a scenario, it would be best to restrict all metal ions, particularly sodium from any medicament to be used in patients with chronic kidney disease.

Thus, there exists a need to develop pharmaceutical compositions which are devoid of the detrimental effects of metal ions particularly the sodium ions. The inventors of the present invention have developed compositions which can be used safely in patients with chronic kidney disease.

OBJECT OF INVENTION

An object of the present invention is to provide pharmaceutical compositions comprising phosphate binding polymers free of added metal ions.

Another object of the invention is to provide pharmaceutical compositions comprising wet granulated Sevelamer carbonate free of added metal ions.

Another object of the invention is to provide pharmaceutical compositions comprising wet granulated Sevelamer carbonate free of crystalline cellulose and/or low substituted hydroxypropyl cellulose and free of reducing sugars.

Yet another object of the invention is to provide pharmaceutical compositions comprising wet granulated Sevelamer carbonate and at least one polyol selected from the group consisting of inositol, sorbitol, mannitol, isomalt, xylitol, lactitol, erythritol and maltitol.

Another object of the invention is to provide pharmaceutical compositions substantially free of monovalent anion other than bicarbonate anion, preferably comprising less than about 0.05% (w/w) of monovalent anion, more preferably less than about 0.05% (w/w) of halides.

Another object of the invention is to provide pharmaceutical compositions of Sevelamer carbonate free of added monovalent anion source.

Yet another object of the invention is to provide pharmaceutical compositions of phosphate binding polymers free of added metal salt of monovalent anion.

SUMMARY OF INVENTION

The present invention provides pharmaceutical composition comprising phosphate binding polymer free of added metal ions and/or added monovalent anion source.

Preferably, the phosphate binding polymer is Sevelamer carbonate. More preferably, Sevelamer carbonate is wet granulated. Preferably, Sevelamer carbonate is present in an amount from about 60% to 90% by weight of total composition. Preferably, the particles of the active ingredient Sevelamer carbonate are spherical or globular/oval in shape.

In one aspect, the invention provides pharmaceutical composition comprising phosphate binding polymer free of added metal ions and/or added monovalent anion source, wherein the metal ions are monovalent, divalent or trivalent and are selected from the group consisting of sodium, potassium, calcium, magnesium and aluminium and the added monovalent anion source is a metal salt of monovalent anion.

In one aspect, the present invention is directed to pharmaceutical compositions; wherein the composition is free of crystalline cellulose and/or low substituted hydroxypropyl cellulose.

In one aspect, the present invention provides pharmaceutical composition comprising wet granulated phosphate binding polymer, preferably Sevelamer carbonate and at least one polyol; said composition having at least one of the following characteristics:

(a) less than about 0.05% (w/w) of monovalent anion other than bicarbonate anion;
(b) free of added metal ions and/or added monovalent anion source;
(c) said composition is a solid dosage form having at most about 90% particles with a particle size not more than about 400 microns but not less than about 45 microns and having a disintegration time of less than 30 minutes.
(d) free of reducing sugars;
(e) free of agents which compete with Sevelamer for phosphate binding activity;
(f) said composition comprises Sevelamer carbonate in an amount of less than about 95% by weight of total composition.

Preferably, the polyol is selected from the group consisting of inositol, sorbitol, mannitol, isomalt, xylitol, lactitol, erythritol and maltitol.

In one aspect, the invention is directed to pharmaceutical composition comprising Sevelamer carbonate substantially free of monovalent anion other than bicarbonate anion. Preferably, said composition comprises less than about 0.05% (w/w) of monovalent anion. More preferably, said monovalent anions are halides such as chlorides.

In another aspect, the invention is directed to pharmaceutical compositions of Sevelamer carbonate characterized in that the composition has a Phosphate Binding Capacity of about 3 mMole/gm to about 7 mMole/gm.

In another aspect, the invention is directed to pharmaceutical compositions characterized in that the composition is free of agents which compete with Sevelamer for the phosphate binding activity.

In another aspect, the invention is directed to pharmaceutical compositions characterized in that the composition is free of reducing sugars.

In one aspect, the invention provides a tablet comprising phosphate binding polymer free of added metal ions and/or added monovalent anion source comprising a core and a coating wherein the phosphate binding polymer is present in an amount of less than about 95% by weight of the core.

In another aspect, the invention provides a tablet comprising phosphate binding polymer free of added metal ions and/or added monovalent anion source comprising a core and a coating wherein the phosphate binding polymer is present in an amount of at least about 95% by weight of the core.

In another aspect, the invention provides a process for preparing wet granulated Sevelamer carbonate comprising the steps of:
(a) providing Sevelamer carbonate;
(b) preparing a mixture of said Sevelamer carbonate and at least one polyol;
(c) granulating said mixture with a granulation liquid comprising at least 60% (w/w) of organic solvent to produce granulated Sevelamer carbonate.

Preferably, wet granulation is carried out by high shear granulation method or spray granulation method. Preferably, the granulation liquid comprises at least one binder and the organic solvent is an alcohol, preferably $C_1$ to $C_4$ alcohol.

In another aspect, the invention provides a process for preparing a tablet comprising phosphate binding polymer free of added metal ions and/or added monovalent anion source comprising a core and a coating wherein the phosphate binding polymer is present in an amount of less than about 95% by weight of the core, said process comprising:
(a) blending the polymer, optionally with one or more additives;
(b) optionally granulating the blend with a granulation liquid;
(c) lubricating the blend;
(d) compressing the blend into tablet;
(e) coating the tablet.

In another aspect, the invention provides a process for preparing a tablet comprising phosphate binding polymer free of added metal ions and/or added monovalent anion source comprising a core and a coating wherein the phosphate binding polymer is present in an amount of at least about 95% by weight of the core, said process comprising:
(a) blending the polymer, optionally with one or more additives;
(b) optionally granulating the blend with a granulation liquid;
(c) lubricating the blend;
(d) compressing the blend into tablet;
(e) coating the tablet.

Additional aspects and/or advantages of the present invention will be evident from the description that follows.

DESCRIPTION OF THE INVENTION

Figure 1:
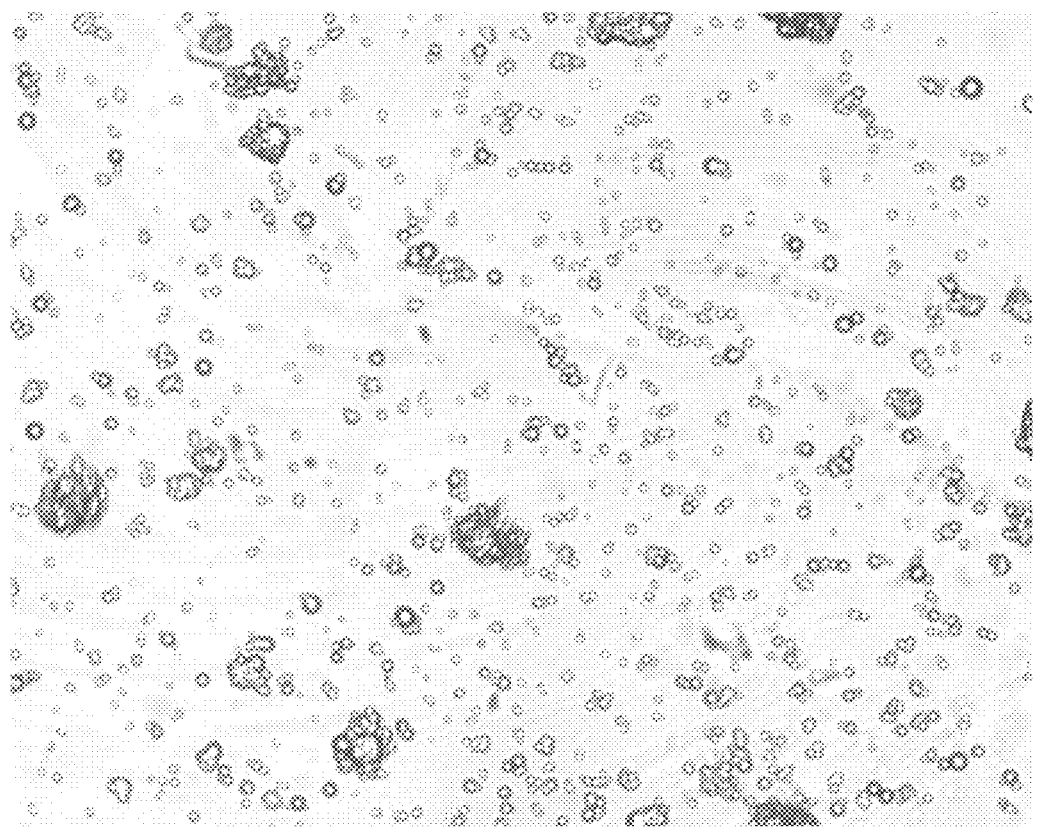
FIG. 1 shows spherical or globular shaped particles of active ingredient Sevelamer carbonate when viewed through a microscope at a magnification of 10×.

The present invention provides pharmaceutical compositions comprising phosphate binding polymers free of added metal ions. The metal ions are monovalent, divalent or trivalent and are selected from the group consisting of sodium, potassium, calcium, magnesium and aluminium.

Accordingly, in one embodiment, the present invention provides pharmaceutical compositions comprising wet granulated Sevelamer carbonate free of added metal ions such as sodium, calcium, potassium, aluminium and magnesium.

In another embodiment, the present invention provides pharmaceutical compositions comprising phosphate binding polymers such as Sevelamer carbonate free of added metal salt of monovalent anion.

Prior art teaches that tablets made from carbonate salts of aliphatic amine polymers suffer from short shelf life and the disintegration time of such tablets increases over time when stored under standard storage conditions which in turn leads to decreased availability of the active components of the drug to a patient. However, prior art tries to solve these problem by incorporating a monovalent anion source to tablets of aliphatic amine carbonate.

These monovalent anion source can be lithium, sodium, potassium, magnesium, calcium, aluminium, lanthanide, or actinide salt of a monovalent anion. However, an incorporation of high amount of monovalent anion source such as lithium, sodium, potassium, magnesium, calcium, aluminium, lanthanide, or actinide salt of a monovalent anion may be detrimental to patients with chronic kidney disease as it poses various risks associated with the increased levels of these metal ions. Health care professionals have recognized the detrimental effects of high sodium intake on blood pressure control, congestive heart failure and fluid balance in patients with chronic kidney disease. High levels of calcium intake poses risks associated with hypercalcemia such as cardiac arrhythmias, renal failure, and skin and visceral calcification.

The inventors of the present invention have successfully developed compositions of aliphatic amine polymers, more particularly compositions of phosphate binding polymers such as Sevelamer carbonate free of added metal ions. Limiting the intake of commonly used metals salts such as those of sodium, calcium, potassium, aluminium or magnesium will benefit the patients with chronic kidney disease and on haemodialysis.

As the compositions are devoid of any ingested calcium, the detrimental effects and risks associated with hypercalcemia such as cardiac arrhythmias, renal failure, and skin and visceral calcification are eliminated.

The inventors have now found a way to prepare pharmaceutical compositions by the choice of certain types of additives. Such compositions are devoid of any adverse effects on patients with chronic kidney disease and are safe for administration to patients with chronic kidney disease.

Pharmaceutical compositions of the present invention are used for the control of serum phosphorus in patients with Chronic Kidney Disease (CKD) on dialysis and also used for the control of serum phosphorus in patients with Chronic Kidney Disease (CKD) not on dialysis.

In another embodiment, the present invention provides pharmaceutical compositions comprising wet granulated Sevelamer carbonate in association with pharmaceutically acceptable additives; wherein the composition is devoid of crystalline cellulose and/or low substituted hydroxypropyl cellulose.

In another embodiment, the present invention provides pharmaceutical compositions comprising wet granulated Sevelamer carbonate and at least one polyol. Diabetes is the leading cause of end-stage renal disease (ESRD) and as the compositions as described herein are for the treatment of patients with chronic kidney disease (CKD) or end-stage renal disease (ESRD), the use of sugars is avoided. In the practice of the present invention, the composition comprises at least one polyol selected from the group consisting of inositol, sorbitol, mannitol, isomalt, xylitol, lactitol, erythritol and maltitol. These polyols are safe for administration to patients with diabetes. Preferred polyol for use in the pharmaceutical composition of the present invention is mannitol and isomalt. Mannitol is the most preferred polyol as it is not absorbed significantly from the gastrointestinal tract on oral administration.

Polyols such as mannitol and isomalt have an advantage of low moisture pick up and satisfactory flow characteristics. Granules containing mannitol get easily dried and have less tendency to pick up moisture. Mannitol is used in an amount of about 0.2% to about 7.0% by weight of the total composition, preferably between 0.4% to 5.0%. Granular and spray dried forms of mannitol are generally used in granulations. Mannitol provides granules which can be easily dried. Sevelamer carbonate being moisture sensitive, mannitol is the preferred diluent as it is not hygroscopic. Various grades of mannitol are available commercially. Preferred grades of mannitol include Pearlitol SD 200 of Roquette, France.

Isomalt is hydrogenated isomaltulose which is an equimolar mixture of 6-O-α-D-glucopyranosido-D-sorbitol (1,6-GPS) and 1-O-α-D-glucopyranosido-D-mannitol-dihydrate (1,1-GPM-dihydrate). Isomalt is a non carcinogenic additive commonly used in pharmaceutical preparations. Isomalt is available in various grades based on the particle size where fine grade viz., GalenIQ 810 is used in the wet granulation. Isomalt is preferably used in the range of about 0.2% to about 7%.

In one embodiment, the present invention provides pharmaceutical compositions comprising aliphatic amine polymer, Sevelamer carbonate in an amount of about 60% to about 90% by weight of total composition.

In another embodiment, the invention provides pharmaceutical compositions comprising hydrated aliphatic amine polymer and in particular hydrated Sevelamer carbonate in an amount of about 70% to about 90% by weight of total composition.

In one embodiment, the present invention provides pharmaceutical compositions comprising phosphate binding polymer such as Sevelamer carbonate substantially free of monovalent anion other than bicarbonate anion.

In a preferred embodiment, the invention provides pharmaceutical compositions comprising Sevelamer carbonate having less than about 0.05% (w/w) of monovalent anion.

In a more preferred embodiment, the invention provides pharmaceutical compositions comprising Sevelamer carbonate having less than about 0.05% (w/w) of halides.

In a more preferred embodiment, the invention provides pharmaceutical compositions comprising Sevelamer carbonate having chloride content less than about 0.05% (w/w).

Although the prior art teaches the need for a monovalent anion source to overcome short shelf life and increasing disintegration time, it has now been surprisingly found that pharmaceutical compositions comprising monovalent anion content less than about 0.05% (w/w) and in particular the chloride content less than about 0.05% (w/w) provides good shelf life.

The disintegration time of the tablets according to the invention does not increase over time. The tablets prepared according to the present invention was studied for disintegration time. Table 1 shows the Disintegration time in minutes for the tablets studied for stability at 40° C. and 75% RH. Disintegration test was performed at 37° C. using 0.1N HCl.

TABLE 1

| | Disintegration Time in 0.1N HCl | |
|---|---|---|
| Time period | Tablets prepared according to the invention | RENVELA ® Sevelamer Carbonate |
| Initial | 8 mins | 8 mins |
| 1 month | 8 mins | 8 mins |
| 2 month | 8 mins | 8 mins |
| 3 month | 8 mins | 8 mins |

In another embodiment, the present invention provides pharmaceutical compositions wherein the composition is free of added metal salt of monovalent anion.

In one embodiment, the present invention provides pharmaceutical compositions free of added monovalent anion source. The inventors of the present invention have successfully developed pharmaceutical compositions of phosphate binding polymers, particularly compositions of Sevelamer carbonate by eliminating the use of any monovalent anion source such as sodium chloride, potassium chloride and the like.

Although prior art states that the addition of a monovalent anion source to Sevelamer carbonate prevents the increase in the disintegration time of the tablets and increases the shelf life, the inventors of the present invention have successfully developed stable formulations of Sevelamer and in particular Sevelamer carbonate by eliminating the incorporation of any monovalent anion source and particularly eliminating the incorporation of sodium chloride. Thus, the pharmaceutical compositions of the present invention are devoid of any added monovalent anion source.

In another embodiment, the present invention provides pharmaceutical compositions characterized in that the composition is free of reducing sugars. Reducing sugars in basic solution, forms aldehyde or ketone and allows the sugar to act as a reducing agent. Some reducing sugars are glucose, fructose, lactose, glyceraldehyde, arabinose and maltose.

Monosaccharides that contain ketone groups are known as ketoses and those which contain aldehyde groups are known as aldoses. Sevelamer contains the amine group which undergoes Maillard reaction in contact with additives that contain reducing sugars. Maillard reaction is well known in the art. The products of Maillard reaction are basically brown pigments. Formation of these brown pigments are indication of chemical instability of the composition.

In another embodiment, the invention provides pharmaceutical compositions characterized in that the composition is free of agents which compete with Sevelamer for the phosphate binding activity. These agents contain the phosphate moiety which compete with the Sevelamer for phosphate binding activity. Such agents include calcium phosphate, dibasic calcium phosphate, tribasic calcium phosphate. Sevelamer is a phosphate binding polymer and any phosphate containing additive may compete for phosphate binding activity of Sevelamer. The inventors of the present invention have found that exclusion of such phosphate containing additives renders a more effective composition.

In another embodiment, the invention is directed to pharmaceutical compositions having a Phosphate Binding Capacity of about 3 mMole/gm to about 7 mMole/gm.

In another embodiment, the present invention provides pharmaceutical compositions comprising wet granulated Sevelamer carbonate in association with pharmaceutically acceptable additives wherein said additive comprises at least one water soluble material in the range of 5.0% to 40.0% by weight of total composition.

According to one embodiment, the compositions of the present invention are free of reducing sugars such as lactose and dextrose. Use of reducing sugars such as lactose and dextrose renders discoloration to the tablets. Tablets containing reducing sugar shows yellowish brown discoloration due to Maillard reaction.

According to another embodiment, the compositions of the present invention are free of phosphate containing moiety such as dibasic calcium phosphate, tribasic calcium phosphate, calcium phosphate. Sevelamer is a phosphate binding polymer and any phosphate containing moiety in a diluent may compete for phosphate binding activity of Sevelamer.

According to one embodiment, the compositions of the present invention comprises Sevelamer carbonate in the range of about 60% to about 90% by weight of total composition. More particularly, Sevelamer carbonate compositions of the present invention may be provided in dose strength of 0.4 gram to 3.0 gram. Tablet dosage forms may be provided in the dose strength of 800 mg. Granules of Sevelamer carbonate for oral suspension may be provided as 0.8 gram per packet or 2.4 gram per packet.

In one embodiment, the pharmaceutical compositions of the present invention comprises about 60.0% to 90.0% by weight of Sevelamer carbonate, about 0.1% to about 10.0% by weight of diluent, about 3.0% to about 15.0% by weight of binder, about 2.0% to about 10.0% by weight of disintegrant, about 0.1% to about 3.0% by weight of lubricants and about 3.0% to about 6.0% by weight of coating agents.

Suitably the dosage forms of the present invention are tablets, capsules or granules that can be produced on a commercial scale.

Study was conducted to determine the Phosphate binding capacity of Sevelamer carbonate. Compositions of the present invention showed a Phosphate binding capacity in the range of 3.0 to 7.0 mMole/gram.

Further the compositions prepared by the process as described herein withstand the accelerated stability conditions of temperature and relative humidity and maintain their physical and chemical integrity at accelerated conditions of stability. Long term stability studies are in progress.

In one embodiment, the invention provides use of the compositions for the manufacture of a medicament for the control of serum phosphorus in patients with chronic kidney disease (CKD) on dialysis.

In one embodiment, the invention provides use of the compositions for the manufacture of a medicament for the control of serum phosphorus in patients with chronic kidney disease (CKD) not on dialysis.

In one embodiment, the present invention provides a method for removal of serum phosphorus, said method comprising administering a therapeutically effective amount of pharmaceutical compositions as described herein to a patient in need thereof.

Sevelamer carbonate used in the present invention may be the commercially available Sevelamer carbonate or may be prepared by any conventional process or by the process as described below, Sevelamer hydrochloride (1.1 Kg) was added into 15.5 L solution of sodium bicarbonate (1.1 Kg $NaHCO_3$ in 14.3 L water). The obtained mixture was stirred at 60-65° C. for 4 hrs. The obtained material was filtered by centrifuge filter. The obtained wet cake was added into 15.5 L solution of sodium bicarbonate (1.1 Kg $NaHCO_3$ in 14.3 L water) and stirring was maintained at 60-65° C. for 4 hrs. The material was filtered by centrifuge filter assembly and obtained wet cake was stirred in 11 L water for 1 hr at 60-65° C. The material was filtered by centrifuge filter. The washings of the wet cake with water were repeated thrice at 60-65° C. The obtained wet cake was dried in air tray dryer (ATD) at about 90-100° C. for 30-36 hrs and LOD was checked after every five hours till LOD was in the range of 5 to 10% to get Sevelamer carbonate (0.995 Kg).

Chloride content: 0.03%,
Phosphate binding capacity: 5.5 mMole/gm,
Carbonate content: 5.1 meq/gm.

Sevelamer carbonate particles obtained by the above process have a particle size distribution such that about 90% particles have a particle size not more than about 400 microns, 50% particles have a particle size not more than about 200 microns and 10% particles have a particle size not more than about 100 microns. Preferably, at most about 90% particles have a particle size not more than about 400 microns but not less than about 45 microns. More preferably, at most about 80% particles have a particle size not more than about 400 microns but not less than about 45 microns.

Sevelamer carbonate was micronized using conventional techniques to obtain the particle size distribution such that about 90% particles have a particle size not more than about 50 microns. More specifically, about 90% particles have a particle size not more than about 50 microns, 50% particles have a particle size not more than about 20 microns, 10% particles have a particle size not more than about 10 microns.

In one embodiment, the present invention provides a pharmaceutical composition comprising wet granulated phosphate binding polymer, preferably Sevelamer carbonate and at least one polyol; said composition having at least one of the following characteristics:
  (a) less than about 0.05% (w/w) of monovalent anion other than bicarbonate anion;
  (b) free of added metal ions and/or added monovalent anion source;
  (c) said composition is a solid dosage form having at most about 90% particles with a particle size not more than about 400 microns but not less than about 45 microns and having a disintegration time of less than 30 minutes.
  (d) free of reducing sugars;
  (e) free of agents which compete with Sevelamer for phosphate binding activity;
  (f) said composition comprises Sevelamer carbonate in an amount of less than about 95% by weight of total composition.

In one embodiment, the invention provides a tablet comprising phosphate binding polymer free of added metal ions and/or added monovalent anion source comprising a core and a coating wherein the phosphate binding polymer is present in an amount of less than about 95% by weight of the core.

In another embodiment, the invention provides a tablet comprising phosphate binding polymer free of added metal ions and/or added monovalent anion source comprising a core and a coating wherein the phosphate binding polymer is present in an amount of at least about 95% by weight of the core.

Compositions of the present invention may be provided as granules, powders, tablets or capsules. The features of the present invention can be extended to aliphatic amine polymers, particularly to phosphate binding polymers other than Sevelamer. Some of the aliphatic amine polymers known in the art include colestipol, cholestryramine, orlistat, colesevelam and the like.

The invention also provides a process for preparation of compositions of Sevelamer carbonate by wet granulation comprising high shear granulation or spray granulation.

In one embodiment, the invention provides a process for preparing wet granulated Sevelamer carbonate, the process comprising the steps of:
(a) providing Sevelamer carbonate;
(b) preparing a mixture of said Sevelamer carbonate and at least one polyol;
(c) granulating said mixture with a granulation liquid comprising at least 60% (w/w) of organic solvent to produce granulated Sevelamer carbonate.

In a preferred embodiment, the invention provides a process for preparing wet granulated Sevelamer carbonate, the process comprising the steps of:
(a) providing Sevelamer carbonate;
(b) preparing a mixture of said Sevelamer carbonate and mannitol;
(c) granulating said mixture with a granulation liquid comprising at least 60% (w/w) of organic solvent to produce granulated Sevelamer carbonate.

In another preferred embodiment, the invention provides a process for preparing pharmaceutical compositions of Sevelamer carbonate comprising wet granulation comprising the steps of:
(a) providing a mixture of Sevelamer carbonate, at least one polyol and optionally one or more diluents;
(b) optionally wetting the above mixture with water or aqueous solution of polyethylene glycol;
(c) preparing a granulation liquid by dissolving binder in an organic solvent or mixture of organic solvent and water;
(d) granulating the mixture of step (a) or step (b) using granulation liquid by high shear granulation or spray granulation to form granules;
(e) formulating the granules into oral dosage forms.

In one embodiment, the invention provides a process for preparation of Sevelamer carbonate compositions comprising high shear granulation comprising the steps of:
(a) providing a mixture of Sevelamer carbonate, at least one polyol and optionally one or more diluents;
(b) optionally wetting the above mixture of step (a) with water or aqueous solution of polyethylene glycol;
(c) preparing a granulation liquid by dissolving binder in an organic solvent or mixture of organic solvent and water;
(d) granulating the mixture of step (a) or step (b) using granulation liquid by high shear granulation to form granulated mass;
(e) drying the granulated mass;
(f) sizing and milling the dried granulated mass using ball mill or fluid energy mill to form granules of suitable size;
(g) blending the milled granules with one or more disintegrants and lubricating the granules;
(h) optionally compressing the lubricated granules into tablets and coating the tablets or filling the lubricated granules into capsules.

In another embodiment, the invention provides a process for preparation of Sevelamer carbonate compositions comprising spray granulation comprising the steps of:
(a) providing a mixture of Sevelamer carbonate, at least one polyol and optionally one or more diluents;
(b) optionally wetting the above mixture of step (a) with water or aqueous solution of polyethylene glycol;
(c) preparing a granulation liquid by dissolving binder in an organic solvent or mixture of organic solvent and water;
(d) spraying the granulation liquid of step (c) onto the mixture of step (a) or step (b) to form uniformly fine granulated mass;
(e) drying the granulated mass;
(f) sizing and milling the dried granulated mass using ball mill or fluid energy mill to form granules of suitable size;
(g) blending the milled granules with one or more disintegrants and lubricating the granules;
(h) optionally compressing the lubricated granules into tablets and coating the tablet or filling the lubricated granules into capsules.

Phosphate binding polymer, Sevelamer carbonate is insoluble in water but swells in contact with water. Due to this tendency of swelling, formulating Sevelamer by wet granulation becomes difficult.

The inventors attempted formulating Sevelamer carbonate by hot melt granulation and hot melt extrusion techniques. However, the results were not satisfactory as very high amount of binder was required and also the granules produced were lacking adequate flow properties.

The inventors of the present invention have been successful in developing a process for wet granulation of Sevelamer carbonate by high shear granulation or spray granulation. High shear granulation can be carried out in rapid mixer granulator or planetary mixer and spray granulation can be carried out in fluid bed processor. High shear wet granulation or wet granulation by spraying as practiced by the present invention improves the cohesiveness of particles and provides excellent flowability and compression characteristics to the tablet. As the granules exhibit good flow properties, tablets produced possess uniformity in weight.

Figure 2:
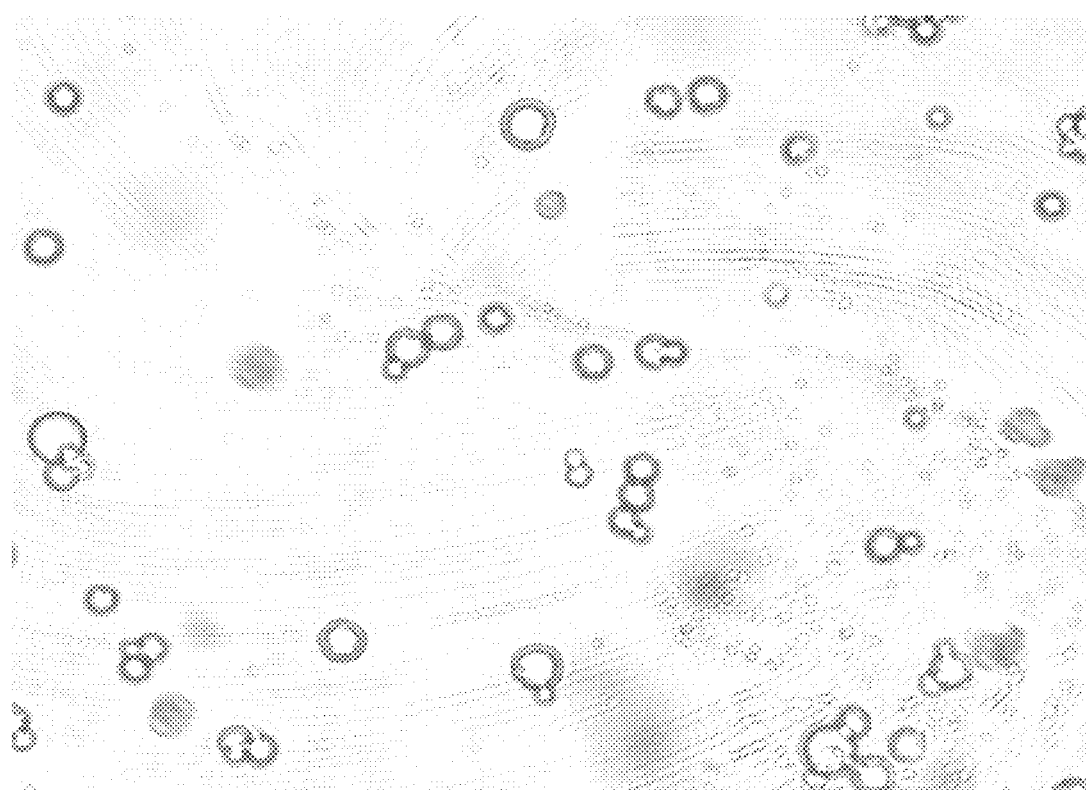
FIG. 2 shows spherical or globular shaped particles of active ingredient Sevelamer carbonate when viewed through a microscope at a magnification of 40×.

In one embodiment, the particles of Sevelamer carbonate are round in shape, particularly spherical or globular/oval in shape (ref. FIG. 1 and FIG. 2). Spherical or globular shaped particles have low bulk density and poor flowability and further resist size reduction. Particles resist deformation and do not rupture or fracture. Due to these characteristics of Sevelamer carbonate, formulating Sevelamer carbonate by direct compression method becomes extremely difficult. In the practice of the present invention; the spherical morphology and hydrophilic nature of active ingredient Sevelamer carbonate presents a special challenge to the formulator.

The process of preparation of Sevelamer carbonate by wet granulation comprises providing a mixture of Sevelamer carbonate, at least one polyol and optionally one or more diluents; wetting said mixture with water; granulating the wet mixture by wet granulation method using a solvent and preferably by using a granulation liquid prepared by dissolving the binder in the solvent; the granulation process being carried out in a rapid mixer granulator. Granulated mass is dried to remove the solvent. Dried granules are further milled or pulverized to get granules size less than 425 microns, preferably less than 250 microns and most preferably below 150 microns using a multi-mill initially and then a fluid energy mill or a ball mill, preferably by using a ball mill. Milled or pulverized granules are blended with one or more disintegrants and lubricated using lubricants known in the art.

Lubricated granules may further be compressed to provide tablets of required size. Compressed tablets may optionally be film coated by non-aqueous coating or aqueous coating or by hydroalcoholic coating.

In a preferred embodiment, the process of preparation of Sevelamer carbonate compositions comprises mixing Sevelamer carbonate, at least one polyol and optionally one or more diluents; wetting said mixture using a solution of polyethylene glycol 6000 (Macrogol) dissolved in water; preparing a granulation liquid by dissolving polyvinyl pyrrolidone (Povidone K-30) in an organic solvent (isopropyl alcohol); granulating the wet mixture using said granulation liquid and drying the granules. Sizing the dried granules through 100# on vibrosifter after milling with multi-mill and ball mill, blending the milled granules with one or more disintegrants and further lubricating with lubricants and compressing the granules. Core tablets may optionally be film coated by aqueous coating process till a weight gain of 4.0% to 6.0% is achieved.

Sevelamer carbonate is a polymeric material with very poor flowability and is bulky. Wetting with water helps in decreasing the interparticulate distance and increasing the contact area between the particles; thus making the Sevelamer carbonate more amenable for the granulation. Wetting is carried out either in a rapid mixer granulator or a planetary mixer or a fluid bed processor. In the practice of the present invention, wetting of mixture of active and diluent is carried out using about 8.0% to 12.0% by weight of water. Alternatively, the mixture of Sevelamer carbonate and diluent may be made wet using a solution of polyethylene glycol dissolved in water. In an alternate method, polyethylene glycol 6000 may be added to the dry mix as a fine powder during the mixing step. Polyethylene glycols of various grades may be used such as polyethylene glycol 6000 or the like. In the practice of the present invention, granulation is carried out by adding the granulation liquid slowly in a thin stream continuously using a peristaltic pump under high speed mixing with the impeller 'on' and chopper 'off'. On complete addition of granulation liquid, continue mixing at high impeller speed till a cohesive granular mass is obtained. If the mass is lumpy then chopper may be used at high speed with impeller also at high speed to obtain uniform wet mass.

Drying of wet mass may be carried out using fluidized bed drier or tray drier. Initial drying is performed without application of temperature so as to remove the organic solvent and further the wet mass is dried for sufficient time at about 45° C. to 50° C. till loss on drying value is achieved in the range of about 8.0% to about 12.0%. If planetary mixer is used for granulation, the wet mass requires milling with a multi-mill using 8.0 mm screen and may then be charged for drying.

In one embodiment, the process comprises mixing Sevelamer carbonate, at least one polyol and optionally one or more diluents; optionally wetting the mixture using water in a rapid mixer granulator; preparing a granulation liquid by dissolving ethyl cellulose in an organic solvent such as isopropyl alcohol; granulating the mixture of Sevelamer carbonate and polyol using said granulation liquid and drying the granules. Sizing the dried granules through 60# on vibrosifter after milling with multi-mill and ball mill and further blending the milled granules with one or more disintegrants and lubricating with lubricants and compressing the granules into tablets. Core tablets may optionally be film coated.

In a preferred embodiment, Sevelamer carbonate is mixed with mannitol and made wet using water; granulated using granulation liquid prepared by dissolving the ethyl cellulose in isopropyl alcohol. Granulation is carried out in a rapid mixer granulator and the granulated mass is dried to remove the organic solvent till loss on drying value in the range of about 8.0% to about 12.0% is achieved. Dried mass is sized using ball mill to achieve granules of required size; blended with one or more disintegrants and further lubricated with lubricants and compressed into tablets.

In another embodiment, the process of preparation of Sevelamer carbonate composition comprises providing a mixture of active ingredient Sevelamer carbonate and one or more additives; granulating the mixture by high shear wet granulation or wet granulation by spraying using a solvent and preferably by using a granulation liquid prepared by dissolving the binder in an organic solvent; the granulation process being carried out in a rapid mixer granulator. Granulated mass is further dried to remove the organic solvent and further dried till a loss on drying value in the range of about 8.0% to about 12.0% is achieved. Dried granules are further milled or pulverized to get granules of size less than 425 microns, preferably less than 250 microns and most preferably 150 microns using a fluid energy mill or a ball mill; preferably by using a ball mill. Milled or pulverized granules are blended with disintegrants and lubricated using lubricants and further compressed to provide tablets of required size or filled into capsules. Compressed tablets may be further coated.

In one embodiment, the granules provided by high shear wet granulation or wet granulation by spraying process as described herein are spherical granules of size less than 425 microns, preferably less than 250 microns and most preferably below 150 microns. Although the dried granulated mass can be milled or pulverized using conventional equipments known in the art such as a multimill, co-mill, cadmill or fitzmill, they have limitations when used for size reduction of Sevelamer carbonate granules. Granule size less than 425 microns (40#), preferably less than 250 microns (60#) and most preferably 150 microns (which passes through 100#) is difficult to obtain using such mills. Large granules pose difficulties during compression by decreasing the compressibility of the granules and produces porous tablets with low hardness which consequently exhibit high friability and pose a risk of moisture uptake during aqueous film coating. Oversized granules retained after milling through 0.5 mm screen on a conventional mill and sifting on a vibrosifter through 60# are milled in a ball mill or fluidized energy mill to obtain particle size less than 250 microns for the granules.

In the practice of the present invention comminution techniques comprise grinding in an air-jet mill/impact mill, fluid energy mill, ball mill, vibration mill, mortar mill or pin mill. According to the invention, size reduction or pulverization using fluid energy mill or ball mill provides spherical granules of size less than 150 microns, which provides an ease in compressibility. Ball milling being the preferred mode for size reduction of granules. In ball milling, the process of size reduction occurs due to combined effect of impact and attrition. In a fluid energy mill, the material is suspended and conveyed at high velocity by air, which is passed through nozzles at 100 to 150 pounds per square inch. The violent turbulence of the air reduces the particle size by interparticulate attrition. Ball mill is preferred in terms of output and productivity for large scale batches.

Milled mass is further sifted through a vibrosifter and oversized particles were milled through a mill preferably a ball mill with stainless steel balls and further sifted through a vibrosifter. Mass is repeatedly milled with ball mill and sifted through vibrosifter till the resultant granules passes through 60#. According to a preferred aspect, granules of the present invention preferably have a particle size of 100% passing through 60#. Particle of size 250 microns or less provides satisfactory compression of granules and further provides elegant non-porous, non-friable tablets with a smooth impervious surface which can withstand the rigours of aqueous film coating.

In the practice of the present invention, the granule size is controlled such that 100% granules passes through 60# which provides tablets which exhibit a smooth impervious surface with a hardness of at least 80 N, friability less than 0.8% and preferably in the range of 0 to 0.5%, disintegration time of about 5 to 10 minutes. By controlling the granule size at less than 425 microns, preferably less than 250 microns (which passes through 60#) elegant tablets are produced, which allows smooth aqueous film coating operation.

In another embodiment, the invention provides a process for preparing a tablet comprising phosphate binding polymer free of added metal ions and/or added monovalent anion source comprising a core and a coating wherein the phosphate binding polymer is present in an amount of less than about 95% by weight of the core, said process comprising:
(a) blending the polymer, optionally with one or more additives;
(b) optionally granulating the blend with a granulation liquid;
(c) lubricating the blend;
(d) compressing the blend into tablet;
(e) coating the tablet.

In another embodiment, the invention provides a process for preparing a tablet comprising phosphate binding polymer free of added metal ions and/or added monovalent anion source comprising a core and a coating wherein the phosphate binding polymer is present in an amount of at least about 95% by weight of the core, said process comprising:
(a) blending the polymer, optionally with one or more additives;
(b) optionally granulating the blend with a granulation liquid;
(c) lubricating the blend;
(d) compressing the blend into tablet;
(e) coating the tablet.

Sevelamer carbonate tablets may be coated by aqueous or non-aqueous or hydroalcoholic coating. Film coating provides an impervious surface and prevents the ingress of moisture from the aqueous coat. Preferably, coating of tablets is done using an aqueous coating method. Aqueous coating of an hydrophilic active ingredient is another difficult process and posed a real challenge to the inventors of the present invention as the Sevelamer has a tendency to swell in presence of water. Aqueous coating has been achieved by having a fine control on the hardness of the cores, which balances the need for a hard core to ensure good coating as well as meet the requirement for disintegration of coated tablets. As the tablet core is hard with an impervious smooth surface, it withstands the aqueous film coating and the polymer Sevelamer carbonate does not swell during coating.

Film coating may be carried out using polymers such as polyvinyl alcohol, hydroxyethyl cellulose, ethylcellulose, hydroxypropyl methyl cellulose, methacrylic acid co-polymers. Ready mix coating materials may comprise plasticizers selected from propylene glycol, triacetin or polyethylene glycol. Coating agents may be used in the range of about 3% to about 8% by weight of total composition. Preferably, the coating composition is devoid of any coloring agent.

Tablets may be compressed using suitable punches and dies. Tablets may be of oval, elliptical, spherical or caplet shape. Compression can be carried out using equipments known in the art such as a rotary tablet press or any compression machine.

Tablets prepared by the process according to the invention meet the specification for disintegration (Limit not more than 30 minutes). Other parameters of tablets such as hardness, friability, and thickness were measured and the results met the standard specifications for tablets.

Compositions of Sevelamer carbonate, particularly the tablets may be packed in aluminium strips or by cold formed blister pack, which is a cold process of blister packing, which acts as an excellent moisture barrier with negligible moisture vapor transmission rate and adequate environmental protection during shelf life.

According to another embodiment, the spherical granules produced by high shear wet granulation or wet granulation by spraying process may be filled along with suitable additives into hard gelatin capsules of suitable size. Capsule filling can be done using any suitable capsule filling machine.

Pharmaceutically acceptable additives that may be used according to the present invention include one or more additives selected from diluents, binders, lubricants, glidants, coating agents, plasticizers and the like. According to the invention, the additives chosen are such that they do not pose any risk for patients with chronic kidney disease.

Diluents are substances which usually provide bulk to the composition. Suitable diluents for use in the pharmaceutical composition of the invention include, but are not limited to maize starch and pregelatinized starch. Preferably, the composition comprises diluents in an amount of about 0.1% to about 10.0% by total weight of the composition. Tablet compositions which uses reducing sugars such as lactose and dextrose as diluents show discoloration as the tablets turn to yellowish brown colour due to Maillard reaction. Similarly dibasic calcium phosphate, tribasic calcium phosphate are also avoided since Sevelamer is a phosphate binding polymer and any phosphate containing diluent may compete for phosphate binding activity of Sevelamer.

Binders impart cohesiveness to tablet formulation and ensures that the tablet remain intact after compression. Suitable binders for use in the pharmaceutical composition of the invention include, but are not limited to hydroxypropyl methyl cellulose, hydroxyethyl cellulose, ethyl cellulose, cellulose derivatives, maize starch, starch derivatives, polyvinylpyrrolidone alone or in combination with polyethylene glycols and the like. Binders may be used in an amount of about 3.0% to about 15.0% by total weight of the composition. Binder preferred in the practice of the present invention is ethyl cellulose or polyvinyl pyrrolidone.

Different grades of ethyl cellulose having various viscosities are commercially available. Ethyl cellulose of specific grades or blends of different grades may be used to obtain solutions of desired viscosity. Ethyl cellulose having viscosity in the range of 4 cps to 22 cps is used; preferred being ethyl cellulose with viscosity of about 5 to 15 cps. Preferred grade of ethyl cellulose used for Sevelamer carbonate tablets is Ethocel EC-N 7 Pharm manufactured by Dow chemical company. Ethyl cellulose is not metabolized following oral consumption and therefore a non-calorific substance. Suitable solvents for preparing the granulation solution include organic solvents such as halogenated hydrocarbon or an alcohol, preferably $C_1$ to $C_4$ alcohols. Suitable solvents include isopropyl alcohol, ethanol or dichloromethane.

Suitable disintegrants for use in the pharmaceutical composition of the invention include, but are not limited to pregelatinised starch and crospovidone. Disintegrants may be used in an amount of about 2.0% to about 10.0% by weight of total composition.

Lubricants are additives that are used to prevent adhesion of the granules/powder material to the manufacturing equipments such as hoppers. Lubricants reduce the interparticle friction and improves the flow of the granules/powder materials and also assist the ejection of the tablet from the tabletting die. Suitable lubricants for use in the pharmaceutical composition of the invention include, but are not limited to glyceryl monostearate, glyceryl behenate, glyceryl palmitostearate, hydrogenated vegetable oil, mineral oil, polyethylene glycol, stearic acid, zinc stearate and the like. Lubricants may be present in an amount of about 0.1% to about 3.0% by weight of total composition.

The present invention further provides use of the compositions of Sevelamer carbonate in the control of serum phosphorus in patients suffering from chronic kidney disease (CKD).

In one embodiment, the present invention provides a method for treating a patient suffering from chronic kidney disease (CKD) comprising administering a therapeutically effective amount of Sevelamer carbonate composition as described herein.

Although the present invention makes use of organic solvents such as isopropyl alcohol for granulation, the organic volatile impurity level in the finished product is quite low and is within the permissible limit. (Limit as per ICH guidelines: 5000 ppm)

As used herein, the term "composition", unless otherwise defined refers to all solid oral pharmaceutical dosage forms that contain aliphatic amine polymers such as tablets, granules, powders, capsules and the like.

As used herein, the term "additives" refers to a pharmaceutically acceptable ingredients that are commonly used in the pharmaceutical technology for preparing oral pharmaceutical dosage forms.

As used herein, the term "therapeutically effective amount" refers to an amount sufficient to cause an improvement in a clinically significant condition in the patient or even prevent a disease, disorder or condition in a patient.

As used herein, the term "tablet" is intended to encompass compressed pharmaceutical dosage formulations of all shapes and sizes, whether coated or uncoated.

The present invention is further illustrated by reference to the following examples which is for illustrative purpose only and does not limit the scope of the invention in any way.

EXAMPLES

Example 1

Sevelamer carbonate (168 g) was co-sifted with mannitol (Pearlitol SD 200) (4 g) and was added to a rapid mixer granulator (RMG). Water (20 g) was then added to it and mixed at impeller speed 100 rpm. Ethyl cellulose (16 g) was dissolved in hot (45° C.) isopropyl alcohol (50 g) and was added to the RMG and the mixture of Sevelamer carbonate and mannitol was granulated at impeller speed 180 rpm without chopper on. Granulated mass was then discharged into bowl of Restch dryer and air dried followed by drying at temperature of about 50° C. Dried mass was milled using multimill/sifter and further using ball mill to obtain granules which passed through 60# S.S. sieve. Granules were blended in a conta blender with Kollidon CLF (12 g) previously sifted through 60# S.S. sieve and further blended with stearic acid (1 g) previously sifted through 60# S.S. sieve. Lubricated granules were compressed on a conventional tableting machine to produce 800 mg tablets of Sevelamer carbonate. Core tablets were film coated by aqueous process till a weight gain in the range of about 4.0% to about 6.0% was achieved.

Example 2

Sevelamer carbonate (420 g) was co-sifted with mannitol (Pearlitol SD 200) (10 g) using 20# stainless steel sieve and was transferred into a rapid mixer granulator and mixed for 5 minutes at 100 rpm. Binder solution was prepared by dissolving povidone in a mixture of isopropyl alcohol and water (65:35). Binder solution was added to the mixture of Sevelamer carbonate and mannitol and was mixed at impeller high speed 180 to 200 rpm with chopper off for sufficient time till a cohesive mass was formed. The mass was air dried for sufficient time in Glatt drier and further dried at temperature of 50° C. to 60° C. till loss on drying value of about 8% to 12% was achieved. Dried granules were sifted through 60# sieve and the over sized granules were milled using ball mill and the milled mass was sifted through 60# sieve. Sifted granules were blended with presifted Kollidon CLF (sifted through 60#) and stearic acid (sifted through 60#) in a conta blender and was compressed on 0.826×0.374 inch capsule shaped punches and dies to obtain tablet having weight of 1130 mg per tablet and hardness of about 80 to 140 N. Compressed tablets were coated using coating solution prepared by dissolving coating ready mix containing HPMC 5 cps and triacetin in water, till weight gain of 4.0. % to 6.0% of the core tablet was achieved.

Example 3

Sevelamer carbonate (840 g) was co-sifted with mannitol (Pearlitol SD 200) (20 g) using 20 mesh S S Sieve on vibrosifter, and loaded into the rapid mixer granulator and was mixed for about 5 minutes. Binder solution was prepared by dissolving about 80 g Ethocel in 400 g Isopropyl alcohol and was added to the dry mix in the rapid mixer granulator which was pre-wetted with water (110 g). Wet mass was air dried in Glatt drier followed by drying at temperature about 50° C. Dried mass was milled using multimill/sifter and further milled using ball mill to obtain granules which passed through 60# S.S. sieve. Granules were blended in a conta blender with pregelatinised starch (70.0 g) previously sifted through 60# S.S. sieve and further blended with stearic acid (1.0 g) previously sifted through 60# S.S. sieve. Lubricated granules were compressed on a conventional tableting machine to produce Sevelamer carbonate tablets 800 mg. Core tablets were film coated by aqueous process till a weight gain in the range of about 4.0% to about 6.0% was achieved.

Example 4

Sevelamer carbonate (420 g) was co-sifted with mannitol (Pearlitol SD 200) (10 g) using 20# stainless steel sieve and transferred into a rapid mixer granulator and mixed for 5 minutes at 100 rpm. A binder solution was prepared by dissolving povidone in a mixture of isopropyl alcohol and water (100:35 g). The binder solution was added to the mixture of Sevelamer carbonate and mannitol and was mixed at impeller high speed 180 to 200 rpm with chopper off condition for sufficient time till a cohesive mass was formed. The mass was air dried for sufficient time in Glatt drier and further dried at temperature of 50° C. to 60° C. till loss on drying value of about 8% to 12% was achieved. Dried granules were sifted through 60# Sieve and the over sized granules were milled using ball mill and the milled mass was sifted through 100# sieve. Sifted granules were blended with presifted pregelatinised starch 1500 (sifted through 60#) and stearic acid (sifted through 60#) in a conta blender and was compressed on 0.826×0.374 inch capsule shaped punches and dies to obtain tablet having weight of 1130 mg per tablet and hardness of about 80 to 140 N. Compressed tablets were coated using coating solution prepared by dissolving coating ready mix containing HPMC 5 cps and triacetin in water, till weight gain of 4.0% to 6.0% of the core tablets was achieved.

Example 5

Sevelamer carbonate (8400 g) was co-sifted with mannitol (Pearlitol SD 200) (250 g) using 20# stainless steel sieve and transferred into a rapid mixer granulator. The mass was mixed for 5 minutes at 100 rpm and further made wet using water (1000 g) was further mixed for 5 minutes. Binder solution was prepared by dispersing ethylcellulose (Ethocel N 7 Pharm) (800 g) in warm isopropyl alcohol (2400 g) at 40-50 deg C. The warm dispersion of ethylcellulose in Isopropyl alcohol was added to the dry mix and mixed at impeller high speed 180 to 200 rpm with chopper off condition for sufficient time till a cohesive mass was formed. The mass was air dried for sufficient time in Glatt drier and further dried at temperature of 50° C. to 60° C. till loss on drying value of about 8% to 12% was achieved. The dried granules were sifted through 60# sieve and the over sized granules were milled using ball mill and the milled mass was sifted through 60# sieve. The sifted granules were blended with pre-sifted (sifted through 60#) crospovidone (Kollidon CLF) (350 g) and stearic acid (sifted through 60#) (100 g) in a conta blender and compressed on 0.826×0.38 inch capsule shaped punches and dies to obtain tablet having weight of 1150 mg per tablet and hardness of NLT 80 N. The compressed tablets were coated using coating solution prepared by dissolving coating ready mix containing hydroxypropyl methyl cellulose (HPMC 5 cps) and triacetin in water, till weight gain of 4.0% to 6.0% of the core tablets was achieved.

Example 6

Sevelamer carbonate (8400 g) was co-sifted with mannitol (Pearlitol SD 200) (250 g) using 20# stainless steel sieve and transferred into a rapid mixer granulator. The mass was mixed for 5 minutes at 100 rpm and further made wet using water (1000 g) and further mixed for 5 minutes. Binder solution was prepared by dispersing ethylcellulose (Ethocel N 7 Pharm) (800 g) in warm isopropyl alcohol (2400 g) at 40-50 deg C. The warm dispersion of ethylcellulose in Isopropyl alcohol was added to the dry mix and mixed at impeller high speed 180 to 200 rpm with chopper off condition for sufficient time till a cohesive mass was formed. The mass was air dried for sufficient time in Glatt drier and further dried at temperature of 50° C. to 60° C. till loss on drying value of about 8% to 12% was achieved. The dried granules were sifted through 60# Sieve and the over sized granules were milled using ball mill and the milled mass was sifted through 60# sieve. The sifted granules were blended with pre-sifted (sifted through 60#) crospovidone (Kollidon CLF) (350 g) and zinc stearate (sifted through 60#) (46 g) in a conta blender and compressed on 0.826×0.38 inch capsule shaped punches and dies to obtain tablet having weight of 1100 mg per tablet and hardness of not less than 80 N. The compressed tablets were coated using coating solution prepared by dissolving coating ready mix containing hydroxypropyl methyl cellulose (HPMC 5 cps) and triacetin in water, till weight gain of 4.0% to 6.0% of the core tablets was achieved (Disintegration time: 10 mins).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. In a pharmaceutical composition consisting essentially of sevelamer combined with pharmaceutically acceptable additive, the improvement comprising: use of pharmaceutically acceptable additive consisting essentially of pharmaceutically acceptable additive which does not provide a source of metal ion or monovalent anion.

2. The composition as claimed in claim 1, wherein the composition comprises wet granulated sevelamer.

3. The composition as claimed in claim 1, wherein the metal ions are monovalent, divalent or trivalent and are selected from the group consisting of sodium, potassium, calcium, magnesium and aluminium and the added monovalent anion source is a metal salt of monovalent anion.

4. A pharmaceutical composition comprising wet granulated sevelamer and at least one polyol, said composition having at least one of the following characteristics:
   (a) less than about 0.05% (w/w) of monovalent anion other than bicarbonate anion;
   (b) free of added metal ions and/or added monovalent anion source;
   (c) said composition is a solid dosage form having sevelamer particles, at most about 90% of said sevelamer particles with a particle size not more than about 400 microns but not less than about 45 microns and having a disintegration time of less than 30 minutes;
   (d) free of reducing sugars;
   (e) free of agents which compete with sevelamer for phosphate binding activity; wherein
   (f) said composition comprises sevelamer in an amount of less than about 95% by weight of total composition.

5. The composition as claimed in claim 4, wherein the polyol is selected from the group consisting of inositol, sorbitol, mannitol, isomalt, xylitol, lactitol, erythritol and maltitol.

6. A pharmaceutical composition consisting essentially of sevelamer carbonate substantially free of monovalent anion other than bicarbonate anion.

7. The composition as claimed in claim 6, wherein said composition comprises less than about 0.05% (w/w) of monovalent anion.

8. The composition as claimed in claim 6, wherein said composition comprises less than about 0.05% (w/w) of halides.

9. The composition as claimed in claim 1, wherein the sevelamer carbonate is present in an amount from about 60% to 90% by weight of total composition.

10. The composition as claimed in claim 1, wherein the composition comprises hydrated sevelamer in an amount of about 70% to 90% by weight of total composition.

11. The composition as claimed in claim 9, wherein the unit dose strength of said sevelamer is from about 0.4 gram to about 3.0 gram.

12. The composition as claimed in claim 1, wherein said composition has a Phosphate Binding Capacity of about 3 mMole/gm to about 7 mMole/gm.

13. The composition as claimed in claim 1, wherein the particles of the active ingredient sevelamer are spherical or globular/oval in shape.

14. The composition as claimed in claim 1, wherein the composition is free of reducing sugars.

15. The composition as claimed in claim 1, wherein the composition is free of agents which compete with sevelamer for phosphate binding activity.

16. The composition as claimed in claim 14, wherein the composition is safe for administration to patients with Chronic Kidney Disease and diabetic patients.

17. A process for preparing wet granulated sevelamer as defined in claim 4, the process comprising the steps of:
 (a) providing sevelamer;
 (b) preparing a mixture of said sevelamer carbonate and at least one polyol;
 (c) granulating said mixture with a granulation liquid comprising at least 60% (w/w) of organic solvent to produce granulated sevelamer.

18. The process as claimed in claim 17, wherein the organic solvent is an alcohol, preferably $C_1$ to $C_4$ alcohol.

19. The process as claimed in claim 17, wherein the mixture is pre-wetted with water or aqueous solution of polyethylene glycol prior to granulation.

* * * * *